United States Patent
Cochran et al.

(12) 
(10) Patent No.: US 6,337,329 B1
(45) Date of Patent: Jan. 8, 2002

(54) OXAZOLIDINONES TO TREAT EYE INFECTIONS

(75) Inventors: Robert J. Cochran, Loveland, OH (US); Charles W. Ford, Portage, MI (US)

(73) Assignee: Pharmacia & UpJohn Company, Kalamazoo, MI (US)

(*) Notice: Subject to any disclaimer, the term of this patent is extended or adjusted under 35 U.S.C. 154(b) by 0 days.

(21) Appl. No.: 09/349,430

(22) Filed: Jul. 7, 1999

Related U.S. Application Data

(60) Provisional application No. 60/092,765, filed on Jul. 14, 1998.

(51) Int. Cl.$^7$ ............................................. A61K 31/535
(52) U.S. Cl. ..................................... 514/235.8; 514/912
(58) Field of Search .............................. 514/235.8, 912

(56) References Cited

U.S. PATENT DOCUMENTS

| | | | |
|---|---|---|---|
| 5,164,510 A | 11/1992 | Brickner | 548/231 |
| 5,231,188 A | 7/1993 | Brickner | 548/221 |
| 5,565,571 A | 10/1996 | Barbachyn et al. | 546/144 |
| 5,627,181 A | 5/1997 | Riedl et al. | 514/236.8 |
| 5,652,238 A | 7/1997 | Brickner et al. | 514/235.8 |
| 5,688,792 A | 11/1997 | Barbachyn et al. | 514/235.5 |
| 5,698,574 A | 12/1997 | Riedl et al. | 514/376 |

FOREIGN PATENT DOCUMENTS

WO  WO97/45447  12/1997  ......... C07K/14/435

OTHER PUBLICATIONS

G. D. Vernimb : "A Furazolidone Aerosol Powder Anti Infect in the Prevention and Treatment of Kerato Conjunctivitis in Cattle and Sheep." VM/Sac, Vet. Med. Small Anim. Clin., (1969) 64 (8), 708–710.

L. George, et al.: "Topically applied furazolidone or parenterally administered oxytetracycline for the treatment of infectious bovine keratonconjunctivitis." Journal of The American Veterinary Medical Association. (May 15, 1988) 192 (10) 1415–22.

Robert A. Hyndiuk: Review of Ophthalmology (Jan. 1997) 94.

K.R. Wilhelmus, et al.: The Investigative Ophthalmology & Visual Science, 37(3) Abstracts 4060–B846 and 4056–B842 (1996).

M.H. Goldstein, et al.: The Investigative Ophthalmology & Visual Science, 39(4) Abstract 4951–B70 and 4950–B701 (1998).

*Primary Examiner*—Zohreh Fay
(74) *Attorney, Agent, or Firm*—Bruce Stein; Austin Zhang

(57) ABSTRACT

The present invention involves a method of treating an ophthalmic infection in a useful warm blooded mammal who is in need of such treatment which comprises topical administration of an ophthalmologically effective amount of an OXAZOLIDINONE.

12 Claims, No Drawings

OXAZOLIDINONES TO TREAT EYE INFECTIONS

CROSS-REFERENCE TO RELATED APPLICATIONS

This application claims the benefit of U.S. provisional application Ser. No. 60/092,765, filed Jul. 14, 1998, under 35 USC §119(e)(i).

BACKGROUND OF THE INVENTION

1. Field of the Invention

The present invention is a method of treating various ophthalmic infections with known pharmaceutically useful oxazolidinone antibacterials.

2. Description of the Related Art

U.S. Pat. Nos. 5,164,510, 5,231,188, 5,565,571, 5,652,238, 5,688,792, 5,698,574 and 5,627,181 all disclose various oxazolidinone antibiotics which are well known to those skilled in the art.

U.S. Pat. No. 5,688,792 discloses various oxazolidinone antibiotics which can be administered orally, parenterally or topically. The topical application being by gel or cream vehicle.

Many of the presentations and posters presented at the May 11–16, 1997 at the Association for Research in Vision and Ophthalmology presented a lot of evidence that resistant microorganisms is becoming a significant problem.

*Review of Ophthalmology*, 94 (January 1997) discloses the use of antibacterial/antibiotic agents for ophthalmic purposes. It discloses that the "big gun" of topical antibiotics is vancomycin but that it is poorly tolerated. It further disclosed that other antibacterial agents such as the two fluoroquinolones, ciprofloxacin and ofloxacin, as well as other agents such as cepharlosporins and an aminoglycoside. It appears that while the agents of choice are the fluoroquinolones that more effective agents are needed and that the fluoroquinolones have the drawback of very rapid de novo resistance development.

The *Investigative Ophthalmology & Visual Science*, 37(3) Abstracts 4060-B846 and 4056-B842 (1996) both disclose that while there was no resistance to ciprofloxacin in gram positive microorganisms in the late 1980's or early 1990's, significant resistance had developed by the mid 1990's.

The *Investigative Ophthalmology & Visual Science*, 39(4) Abstract 4951-B70 and 4950-B701 (1998) both disclose problems with decreased susceptibility (increased resistance) of *S. aureus* because of the use of broad spectrum antibiotics in treating ophthalmic infections. This makes it more difficult for physicians to treat eye infections.

SUMMARY OF INVENTION

Disclosed is a method of treating an ophthalmic infection in a useful warm blooded mammal who is in need of such treatment which comprises topical administration of an ophthalmologically effective amount of an OXAZOLIDINONE.

DETAILED DESCRIPTION OF THE INVENTION

The method of the present invention is a method of treating an ophthalmic infection in a useful warm blooded mammal who is in need of such treatment which comprises topical administration of an ophthalmologically effective amount of an OXAZOLIDINONE.

U.S. Pat. No. 5,688,792 which disclosed various oxazolidinone antibiotics disclosed they could be administered orally, parenterally or topically. There are a number of antibacterial agents which can be used topically but are much too toxic to be used ophthalmologically to treat bacterial infections of the eye.

Useful warm blooded mammals which are within the scope of the present invention include humans, pets such as dogs, cats and commercially important mammals such as horses, cattle, pigs. It is preferred that the mammal be a human, dog, or cat; more preferably a human.

The OXAZOLIDINONEs of the present invention are known, see EXAMPLES 1 thru 5 (OXAZOLIDINONEs). It is preferred that the OXAZOLIDINONE be selected from the group consisting of (S)-N-[[3-[3-fluoro-4-[4-(hydroxyacetyl)-1-piperazinyl]-phenyl]-2-oxo-5-oxazolidinyl]methyl]acetamide, (S)-N-[[3-[3-fluoro-4-(4-morpholinyl)phenyl]-2-oxo-5-oxazolidinyl]methyl]acetamide, N-((5S)-3-(3-fluoro-4-(4-(2-fluoroethyl)-3-oxopiperazin-1-yl)phenyl)-2-oxooxazolidin-5-ylmethyl)acetamide, (S)-N-[[3-[5-(3-pyridyl)thiophen-2-yl]-2-oxo-5-oxazolidinyl]methyl]acetamide and (S)-N-[[3-[5-(4-pyridyl)pyrid-2-yl]-2-oxo-5-oxazolidinyl]methyl]acetamide hydrochloride; it is more preferred that the OXAZOLIDINONE be selected from the group consisting of:

(S)-N-[[3-[3-fluoro-4-[4-(hydroxyacetyl)-1-piperazinyl]-phenyl]-2-oxo-5-oxazolidinyl]methyl]acetamide and (S)-N-[[3-[3-fluoro-4-(4-morpholinyl)phenyl]-2-oxo-5-oxazolidinyl]methyl]acetamide. It is even more preferred that the OXAZOLIDINONE be (S)-N-[[3-[3-fluoro-4-(4-morpholinyl)phenyl]-2-oxo-5-oxazolidinyl]methyl]acetamide.

Ophthalmic infections in this invention refer to inflammation of the conjunctiva (conjunctivitis) by staphylococci, streptococci and enterococci, and inflammation of the cornea (keratitis) caused by the same organisms and corneal ulcers. Bacterial conjunctivitis is the most common form of infectious conjunctivitis and bacterial keratitis accounts for 65–90% of all bacterial corneal infections. It is preferred that the ophthalmic infection be bacterial keratitis and bacterial conjunctivitis.

The gram positive microorganisms which cause the ophthalmic infections treated by the OXAZOLIDINONEs of the present invention include Staphylococci, Streptococci, Euterococci, Bacilluis, Corynebacterium, Chlamydia and Neisseria. It is preferred that the microorganism be a Staphylococci, Streptococci or Enterococci. It is more preferred that the infection be caused by Staphylococci and/or Streptococci. The important species of these genus are *Staphloccus aureus*, *Streptococcus viridans*, *Staphloccus epidermidis* and *Streptococcus pneumoniae*. The OXAZOLIDINONEs of the present invention also treat gram positive and gram negative infections caused by anaerobes such as *Bacteroides fragilis*.

The ophthalmic infections are treated by administering the desired OXAZOLIDINONE(s) directly to the eye by use of a pharmaceutical formulation consisting of a solution, cream, ointment, emulsion, suspension and slow release formulations. It is preferred that the pharmaceutical formulation be a solution, cream, ointment, emulsion and suspension; it is more preferred that the ophthalmic pharmaceutical formulation be solution. It is preferred that the ophthalmologically effective amount of the OXAZOLIDINONE for treatment of ophthalmic infections is from about 0.3% to about 20%, it is more preferred that the ophthalmologically effective amount be from about 0.5% to about 18%. It is even more preferred that the ophthalmologically effective amount be from about 6% to about 16%. The OXAZOLIDINONE should be administered in the pharmaceutical formulation two thru four times daily for 7 thru 10 days or until the infection is gone. It is preferable if about 0.03 to about 2.0 ml of the ophthalmic pharmaceutical formulation containing the OXAZOLIDINONE is used each time it is administered. It is more preferable if about 0.05 (about 1 drop) to about 0.25 ml (about 5 drops) is administered.

International Publication WO96/06581 discloses a treatment fluid container having at least one opening of sufficient diameter and where the fluid is under sufficient pressure to discharge the solution as discrete jets and/or droplets. These known treatment fluid containers are useful in administering solutions containing the OXAZOLIDINONE(s). Inserts are also useful for administration of solutions of OXAZOLIDINONE(s) to the eye.

In the method of the present invention, the OXAZOLIDINONEs can be used either individually or in combination with each other. Further, they can be used in combination with other antibacterial agents. In addition, the OXAZOLIDINONEs can be used with non-antibacterial agents in treating the infections of this invention.

The exact dosage and frequency of administration depends on the particular OXAZOLIDINONE used, the particular condition being treated, the severity of the condition being treated, the age, weight, general physical condition of the particular patient, other medication the individual may be taking as is well known to those skilled in the art and can be more accurately determined by measuring the blood level or concentration of the OXAZOLIDINONE in the patient's blood and/or the patient's response to the particular condition being treated.

Definitions

The definitions and explanations below are for the terms as used throughout this entire document including both the specification and the claims.

All temperatures are in degrees Centigrade.

THF refers to tetrahydrofuran.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

Ether refers to diethyl ether.

TLC refers to thin-layer chromatography.

When solvent pairs are used the ratios of solvents used are volume/volume (v/v).

When the solubility of a solid in a solvent is used the ratio of the solid to the solvent is weight/volume (wt/v).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

OXAZOLIDINONE refers to the compounds of EXAMPLES 1 thru 5 of the present invention.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

(S)-N-[[3-[3-Fluoro-4-[4-(hydroxyacetyl)-1-piperazinyl]-phenyl]-2-oxo-5-oxazolidinyl]methyl] acetamide (S)-N-[[3-[3-Fluoro-4-[4-(hydroxyacetyl)-1-piperazinyl]-phenyl]-2-oxo-5-oxazolidinyl]methyl]acetamide is known, see U.S. Pat. 5,652,238, EXAMPLE 1.

Example 2

(S)-N-[[3-[3-Fluoro-4-(4-morpholinyl)phenyl]-2-oxo-5-oxazolidinyl]methyl]acetamide (S)-N-[[3-[3-Fluoro-4-(4-morpholinyl)phenyl]-2-oxo-5-oxazolidinyl]methyl]acetamide is known, see U.S. Pat. 5,688,792, EXAMPLE 5.

Example 3

N-((5S)-3-(3-Fluoro-4-(4-(2-fluoroethyl)-3-oxopiperazin-1-yl)phenyl)-2-oxooxazolidin-5-ylmethyl)acetamide N-((5S)-3-(3-Fluoro-4-(4-(2-fluoroethyl)-3-oxopiperazin-1-yl)phenyl)-2-oxooxazolidin-5-ylmethyl) acetamide is known, see International Publication WO97/27188 (Example 4).

1-t-Butoxycarbonyl-3-oxopiperazine (21.6 g) is dissolved in dry DMF (500 ml) and potassium t-butoxide (24.2 g) is added. The mixture is stirred at 20–25° for 30 minutes, then 1-(4-methylphenylsulfonyloxy)-2-fluoroethane (J. Med. Chem., 23(9), 985–90 (1980), 25.9 g) is added and stirring continued at the same temperature for 24 hours. The solvent is removed and the residue partitioned between ethyl acetate and water. The organic phase is washed with water and concentrated. The residue is dissolved in isopropanol and diluted with iso-hexane forming a precipitate which is removed by filtration. The mixture is chromatoraphed (silica: eluting with a gradient increasing in polarity from 0 to 50% isopropanol in iso-hexane) to give 1-t-butoxycarbonyl-4-(2-fluoroethyl)-3-oxopiperazine.

1-t-Butoxycarbonyl-4-(2-fluoroethyl)-3-oxopiperazine (6.65 g) is dissolved in dichloromethane (500 ml), cooled in an ice-bath and trifluoroacetic acid (150 ml) added. The mixture is stirred at the same temperature for 2 hours. The solvent is removed to give a crude product which is dissolved in the minimum volume of ethyl acetate. Slow addition of ether causes precipitation of 1-(2-fluoroethyl)-2-oxopiperazine as the mono trifluoroacetic acid salt.

1-(2-Fluoroethyl)-2-oxopiperazine trifluoroacetate (6.1 g) is dissolved in acetonitrile (100 ml). N,N-Diisopropylethylamine (13 ml) is added to the mixture, followed by 3,4-difluoronitrobenzene (3.39 g) and the mixture heated to reflux for 18 hours. The solvent is removed and the residue chromatographed (silica; eluting with a gradient increasing in polarity from 0 to 4% methanol in dichloromethane) to give 3-fluoro-4-(4-{2-fluoroethyl}-3-oxopiperazin-1-yl)nitrobenzene.

3-Fluoro-4-(4-{2-fluoroethyl}-3-oxopiperazin-1-yl) nitrobenzene (4.35 g) is dissolved in a mixture of ethyl acetate (250 ml) and DMF (5 ml), and the solution flushed with argon. Palladium (10% on carbon, 200 mg) is added and the mixture hydrogenated under ambient pressure. After gas uptake had ceased, the mixture is filtered through celite and solvent removed. The residue is taken up in ethyl acetate, washed twice with water, dried over magnesium sulfate and the solvent is removed to five 5-amino-2-[4-(2-fluoroethyl)-3-oxopiperazin-1-yl]fluorobenzene which is used without further purification.

5-Amino-2-(4-[2-fluoroethyl]-3-oxopiperazin-1-yl) fluorobenzene (2.6 g) is dissolved in dry dichloromethane (50 ml) under argon. Pyridine (1.03 ml) is added, and the mixture cooled to −20°. Benzyl chloroformate (1.6 ml) is added and the mixture stirred for 10 minutes at −20°, before allowing the temperature to rise to 20–25° over 1.5 hours. The solvents are removed and the residue is dissolved in dichloromethane and washed with sodium bicarbonate solution. After drying over magnesium sulfate and removal of the solvent, the residue is chromatographed (silica, eluting with a gradient increasing in polarity from 0 to 5% methanol in dichloromethane) to give 5-benzyloxycarbonylamino-2-(4-[2-fluoroethyl]-3-oxopiperazin-1-yl)fluorobenzene.

A solution of lithium t-butoxide is prepared by addition of n-butyllithium (1.6 M in hexane, 2.9 ml) to a stirred solution of t-butanol (0.43 g) in anhydrous THF (10 ml) at −10° under argon. After cooling to −70°, a solution of 5-benzyloxycarbonylamino-2-(4-[2-fluoroethyl]-3-oxopiperazin-1-yl)fluorobenzene (1.5 ml) in dry THF (15 ml) is added. After 10 minutes, (R)-glycidylbutyrate (0.67 g) in dry THF (15 ml) is added to the resulting mixture, and stirring continued at −70° for 15 minutes, before allowing the temperature to rise to 20–25° over 16 hours. Methanol (10 ml) is added. Followed by saturated sodium bicarbonate solution (20 ml) and water (10 ml). The organic phase is separated and extracted into ethyl acetate (3×25 ml), washed with saline and dried over magnesium sulfate. The solvent is removed and the residue purified by chromatography (silica; eluting with a gradient increasing in polarity from 0 to 3% methanol in dichloromethane) to give (5R)-3-(3-fluoro-4-[4-(2-fluoroethyl)-3-oxopiperazin-1-yl]phenyl)-5-hydroxymethyloxazolidin-2-one.

(5R)-3-(3-Fluoro-4-[4-(2-fluoroethyl)-3-oxopiperazin-1-yl]phenyl)-5-hydroxymethyloxazolidin-2-one (0.8 g) is dissolved in pyridine (15 ml) and the mixture cooled to 0°. Triethylamine (0.38 ml) and methanesulfonyl chloride (0.19 ml) are added to the mixture, and stirring continued at 20–25° for 2 hours. The solvent is removed and the residue dissolved in dichloromethane, washed with water, saline, dried over magnesium sulfate and concentrated. The resulting residue is triturated with ether to give (5R)-3-(3-fluoro-4-[4-(2-fluoroethyl)-3-oxopiperazin-1-yl]phenyl)-5-(methanesulfonyloxymethyl)oxazolidin-2(0.76 g) which is used without further purification. (5R)-3-(3-Fluoro-4-[4-(2-fluoroethyl)-3-oxopiperazin-1-yl]-5-(methanesulfonyloxymethyl)oxazolidin-2-one (719 mg) is dissolved in dry DMIF (15 ml) and sodium azide (647 mg) is added to the mixture. The mixture is heated at 80° for 6 hrs and then concentrated to dryness. The resulting residue is dissolved in ethyl acetate, washed twice with water, and dried over magnesium sulfate. Removal of the solvent gives (5R)-5-azidomethyl-3-(3-fluoro-4-(4-(2-fluoroethyl)-3-oxopiperazin-1-yl)phenyl)oxazolidin-2-one (413 mg) which is used without further purification.

(5R)-5-Azidomethyl-3-(3-fluoro-4-[4-(2-fluoroethyl)-3-oxopiperazin-1-yl]phenyl)oxazolidin-2-one (360 mg) is dissolved in dry DMF (20 ml) and the mixture purged with argon. Palladium (10% on carbon, 72 mg) is added, followed by acetic anhydride (0.17 ml) and the mixture stirred at 20–250° under hydrogen confined in a balloon for 3 hr. The mixture is filtered through celite, concentrated to dryness and partitioned between ethyl acetate and water. The organic extract is washed with saline, dried over magnesium sulfate and concentrated. The residue is chromatographed (silica gel; eluting with a gradient increasing in polarity from 0 to 2.5% methanol/dichloromethane). The appropriate fractions are pooled and concentrated to (give the title compound.

Example 4

(S)-N-[[3-[5-(3-Pyridyl)thiophen-2-yl]-2-oxo-5-oxazolidinyl]methyl]acetamide (S)-N-[[3-[5-(3-Pyridyl)thiophen-2-yl]-2-oxo-5-oxazolidinyl]methyl]acetamide is known, see U.S. Pat. No. 5,698,574 (Example 124).

Example 5

(S)-N-[[3-[5-(4-Pyridyl)pyrid-2-yl]-2-oxo-5-oxazolidinyl]methyl]acetamide hydrochloride (S)-N-[[3-[5-(4-Pyridyl)pyrid-2-yl]-2-oxo-5-oxazolidinyl]methyl]acetamide hydrochloride is prepared following the general procedure of U.S. Pat. No. 5,627,181 EXAMPLEs 36 and 52 and making non-critical variations but using a 4-pyridinyl adduct.

Example 6

Bacterial Keratitis

A 32 year old male presents complaining of eye pain when blinking and b blurred vision. Upon examination the cornea appears subtly less transparent to the physician than normal cornea and may have actual ulcers in its surface. The diagnosis is infectious keratitis of bacterial etiology which is confirmed by laboratory findings. The physician prescribes a 10% solution of (S)-N-[[3-[3-fluoro-4-(4-morpholinyl) phenyl]-2-oxo-5-oxazolidinyl]methyl]acetamide and instructs the patient to drop 3–5 drops of the solution onto the surface of the eye four times daily for 7 days.

Example 7

Bacterial Conjunctivitis

A ten year old female presents complaining of reddened and swollen eyelids and the presence of mucoid secretions on the eye which interfere with vision. The diagnosis is conjunctivitis and the physician prescribes an oxazolidinone solution which contains 12% of (S)-N-[[3-[3-fluoro-4-(4-morpholinyl)phenyl]-2-oxo-5-oxazolidinyl]methyl] acetamide and instructs the patient to drop 3 drops onto the surface of the eye three times daily for 10 days.

What is claimed is:

1. A method of treating an ophthalmic infection in a human who is in need of such treatment which comprises topical administration of an ophthalmologically effective amount of (S)-N-[[3-[3-fluoro-4-(4-morpholinyl)phenyl]-2-oxo-5-oxazolidinyl]methyl]acetamide.

2. A method of treating an ophthalmic infection according to claim 1 where the OXAZOLIDINONE is administered in a pharmaceutical formulation selected from the group consisting of a solution, cream, ointment, emulsion, suspension and slow release formulations.

3. A method of treating an ophthalmic infection according to claim 2 where the OXAZOLIDINONE is administered in a pharmaceutical formulation selected from the group consisting of a solution, cream, ointment, emulsion and suspension.

4. A method of treating an ophthalmic infection according to claim 2 where the solution is administered in an insert or treatment fluid container.

5. A method of treating an ophthalmic infection according to claim 1 where the OXAZOLIDINONE is administered from 2 thru 4 times daily.

6. A method of treating an ophthalmic infection according to claim 1 where the ophthalmologically effective amount is from about 0.3% to about 20%.

7. A method of treatings an ophthalmic infection according to claim 6 where the ophthalmologically effective amount is from about 0.5% to about 18%.

8. A method of treating an ophthalmic infection according to claim 1 where the infection is caused by Staphylococci, Streptococci, Enterococci, Bacillus, Corynebacterium, Chlamydia and Neisseria.

9. A method of treating an ophthalmic infection according to claim 8 where the infection is caused by Staphylococci, Streptococci and Enterococci.

10. A method of treating an opthalmic infection according to claim 9 where the infection is caused by Staphylococci and Streptococci.

11. A method of treating an ophthalmic infection according to claim 1 where the ophthalmic infection is selected from the group consisting of bacterial keratitis, bacterial conjunctivitis and corneal ulcers.

12. A method of treating an ophthalmic infection according to claim 11 where the ophthalmic infection is bacterial keratitis and bacterial conjunctivitis.

* * * * *